(12) United States Patent
Cheng et al.

(10) Patent No.: US 9,770,166 B2
(45) Date of Patent: Sep. 26, 2017

(54) CONTACT-TYPE OPHTHALMOSCOPE

(71) Applicant: Medimaging Integrated Solution, Inc., Hsinchu (TW)

(72) Inventors: Chu-Ming Cheng, Hsinchu (TW); Long-Sheng Liao, Hsinchu (TW); Ming-Hsien Hsieh, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 12 days.

(21) Appl. No.: 14/680,625

(22) Filed: Apr. 7, 2015

(65) Prior Publication Data

US 2016/0113487 A1 Apr. 28, 2016

(30) Foreign Application Priority Data

Oct. 24, 2014 (TW) .............................. 103136830 A

(51) Int. Cl.
*A61B 3/14* (2006.01)
*A61B 3/00* (2006.01)
*A61B 3/12* (2006.01)
*A61B 3/125* (2006.01)

(52) U.S. Cl.
CPC .......... *A61B 3/1208* (2013.01); *A61B 3/0041* (2013.01); *A61B 3/125* (2013.01); *A61B 3/1225* (2013.01); *A61B 3/14* (2013.01)

(58) Field of Classification Search
CPC ..... A61B 3/1208; A61B 3/125; A61B 3/1225; A61B 3/14; A61B 3/0041
USPC .................................................. 351/206, 219
See application file for complete search history.

(56) References Cited

U.S. PATENT DOCUMENTS

2012/0050683 A1* 3/2012 Yates .................. A61B 3/1208
351/219

* cited by examiner

*Primary Examiner* — Jack Dinh
(74) *Attorney, Agent, or Firm* — Muncy, Geissler, Olds & Lowe, P.C.

(57) ABSTRACT

A contact-type ophthalmoscope includes a contact lens, an annular illumination module, an imaging lens group and an image capture module. The contact lens having a concave surface is configured for contacting an eyeball. The annular illumination module arranged close to the contact lens is configured for providing a direct illumination light source to illuminate a fundus of the eyeball. The imaging lens group is disposed in the central hollow portion of the annular illumination module and configured for converging the reflected light from the fundus of the eyeball. The image capture module is configured for capturing the reflected light converged by the imaging lens group to form an image. The above-mentioned contact-type ophthalmoscope has advantages of better illumination efficiency, compactness and less scattered light reflected from the imaging lens.

17 Claims, 2 Drawing Sheets

CONTACT-TYPE OPHTHALMOSCOPE

BACKGROUND OF THE INVENTION

1. Field of the Invention

The present invention relates to an ophthalmoscope, particularly to a contact-type ophthalmoscope.

2. Description of the Prior Art

The ophthalmoscope is an instrument for inspecting the fundus of an eyeball, including the retina, the optic disc, and the vasculature. However, the conventional non-contact-type ophthalmoscope is limited by the pupil and has a smaller observation area, normally only having a half-viewing angle of about 20 degrees. If the non-contact-type ophthalmoscope requires a larger observation area, the imaging system and illumination system thereof need special designs, such as enlarged lenses or an independent illumination system. However, the special design makes it difficult to reduce the volume of the non-contact-type ophthalmoscope. Since observation of the contact-type ophthalmoscope is performed close to the pupil, a larger observation area is thus obtained.

A conventional contact-type ophthalmoscope adopts an illumination system coaxial with the imaging system. However, it is difficult for the system to avoid the central reflected light from the lenses resulted in influenced observation. Further, the illumination range of the system is proportional to the size of lenses. Therefore, the system has to adopt larger lenses to achieve a larger illumination field. Another conventional contact-type ophthalmoscope adopts optical fibers for conducting light for illumination. It is understood that, due to a smaller light output angle of the optical fiber, it requires a plurality of optical fibers at different directions to provide a larger illumination field but results in complicated structure and increased fabrication cost. Further, the coupling of the light sources and the optical fibers also affects the utilization efficiency of the light source.

Accordingly, it is now a current goal to provide a larger illumination field for the contact-type ophthalmoscope with a simple structure.

SUMMARY OF THE INVENTION

The present invention provides a contact-type ophthalmoscope, which makes the light source offset from the optical axis of the imaging system close to the pupil as much as possible such that the illumination field may be enlarged by using the direct illumination light sources.

A contact-type ophthalmoscope according to one embodiment of the present invention comprises a contact lens, an annular illumination module, an imaging lens group, and an image capture module. The contact lens has a first surface and a second surface opposite to the first surface. The first surface is a concave surface configured for contacting an eyeball. The annular illumination module is arranged close to the second surface of the contact lens and configured for projecting a direct illumination light source passing through the pupil to illuminate the fundus of the eyeball, wherein all or most of light generated by the direct illumination light source is directly incident onto the fundus of the eyeball without reflection by any artificial manipulation surface. The imaging lens group is disposed in the central hollow portion of the annular illumination module to converge the reflected light from the fundus of the eyeball, wherein the central hollow portion of the annular illumination module has an inner diameter of 6-10 mm. The image capture module is configured for capturing the reflected light converged by the imaging lens group to form an image.

Below, the embodiments are described in detail in cooperation with the attached drawings to make easily understood the objectives, technical contents, characteristics and accomplishments of the present invention.

DESCRIPTION OF THE PREFERRED EMBODIMENT

Figure 1:
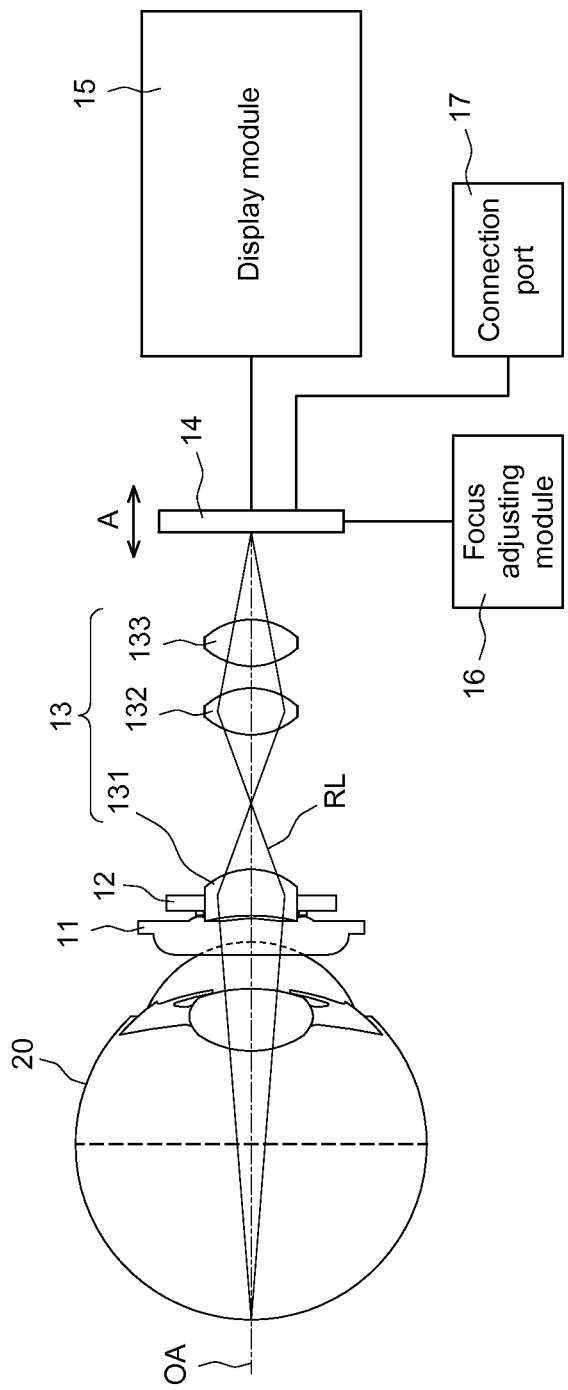
FIG. 1 schematically shows a contact-type ophthalmoscope according to one embodiment of the present invention.
Figure 2:
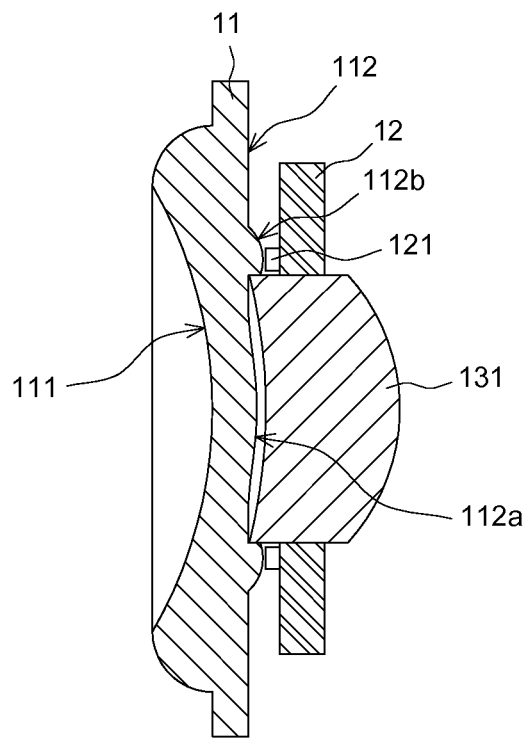
FIG. 2 schematically shows a contact lens, an annular illumination module and a first lens group of a contact-type ophthalmoscope according to one embodiment of the present invention.
Figure 3:
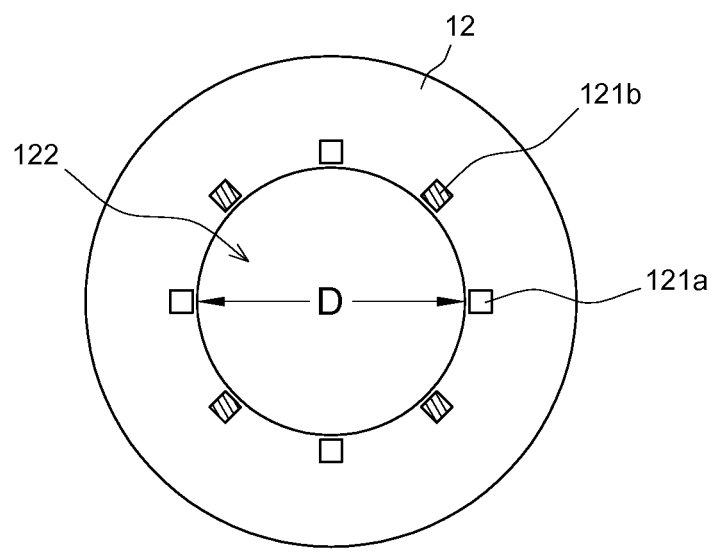
FIG. 3 schematically shows an annular illumination module of a contact-type ophthalmoscope according to one embodiment of the present invention.

Refer to FIGS. 1-3, the contact-type ophthalmoscope according to one embodiment of the present invention comprises a contact lens 11, an annular illumination module 12, an imaging lens group 13, and an image capture module 14. The contact lens 11 has a first surface 111 and a second surface 112 opposite to the first surface 111. The first surface 111 faces an eyeball 20 and contacts the eyeball 20. It is easily appreciated that the first surface 111 is preferably a concave surface to contact the cornea of the eyeball 20. For example, the concave surface has a curvature about identical to the curvature of the cornea. In one embodiment, the contact lens 11 is made of a polymeric material. For example, the contact lens 11 is made of a soft biocompatible polymeric material. Preferably, the contact lens 11 is made of a hydrous polymeric material, such as a silicone hydrogel, an artificial polymer, or a natural resin.

The annular illumination module 12 is arranged close to the second surface 112 of the contact lens 11 and configured for projecting a direct illumination light source passing through the pupil to illuminate the fundus of the eyeball 20. It should be noted that the direct illumination light source refers to all or most of the light generated by the light source is directly incident onto the fundus of the eyeball 20 without reflection by any artificial manipulation surface. In one embodiment, the annular illumination module 12 is a group of light emitting elements 121, such as light emitting diodes (LED), arranged symmetrically to form an annular shape, or an annular light emitting element, such as an organic light emitting diode (OLED). In one embodiment, the annular illumination module 12 has a plurality of first LEDs 121a and a plurality of second LEDs 121b. The first LEDs 121a are symmetrically and annularly arranged, and the second LEDs 121b are also symmetrically and annularly arranged. The central wavelength of the light emitted by the first LEDs 121a is different from the central wavelength of the light emitted by of the second LEDs 121b. For example, the first LEDs 121a emit visible light, such as white light, and the second LEDs 121b emit infrared light for various observations, respectively.

The imaging lens group 13 is disposed in a central hollow portion 122 of the annular illumination module 12 and configured to converge reflected light (RL) from the fundus of the eyeball 20 and form an image on the image capture module 14. In one embodiment, the imaging lens group 13 has a first lens group 131, a second lens group 132 and a third lens group 133, which are arranged in sequence from the eyeball 20 to the image capture module 14. The first lens group 131 is arranged in the central hollow portion 122 of the annular illumination module 12 and configured for converge the reflected light from the fundus of the eyeball 20 and form an intermediate image between the first lens group 131 and the second lens group 132. In one embodiment, the second surface 112 of the contact lens 11 has a convex surface 112a corresponding to the first lens group 131 of the imaging lens group 13. Thereby, the contact lens 11 also contributes a portion of the imaging function. The second lens group 132 is used for overcoming large-viewing-angle distortion. In one embodiment, the second lens group 132 has at least two aspherical lenses. The third lens group 133 is used for eliminating chromatic aberration. In one embodiment, the third lens group 133 has at least two cemented doublet lenses, or a combination of a cemented doublet lens and a cemented triplet lens. In one embodiment, at least one of the second lens group 132 and the third lens group lens 133 is designed to be movable with respect to the first lens group 131. For example, at least one of the second lens group 132 and the third lens group lens 133 are movable along or about with respect to the optical axis OA of the imaging lens group 13. The image capture module 14 captures the reflected light converged by the imaging lens group 13 to form an image. The image capture module 14 includes CCD (Charge Coupled Device), a CMOS (Complementary Metal Oxide Semiconductor) sensor, or a photographic film.

According to the above-mentioned structure, the annular illumination module 12 may approach the eyeball 20 as much as possible to provide an illumination field having an enlarged angle, i.e. the rear half of the eyeball 20 (the left portion of the dotted line shown in FIG. 1). It is easily appreciated that light emitting elements 121 move toward the optical axis OA of the imaging lens group 13 can result in better illumination efficiency but will constrain the space for arranging the first lens group 131 and thus affect the image quality. On the Contrary, the light emitting elements 121 move away from the optical axis OA of the imaging lens group 13 can result in increased space for accommodate a larger-size first lens group 131 but will impair providing uniform illumination. In a preferred embodiment, the inner diameter D of the central hollow portion 122 of the annular illumination module 12 ranges from 6 mm to 10 mm. In other words, the maximum diameter of the first lens group 131 ranges from 6 mm to 10 mm.

In one embodiment, the LEDs of the light emitting elements 121 may adopt a simple package structure for the light emitting elements 121 to approach the optical axis OA. In other words, the packaged LED is provided with no secondary optical element that is capable of deflecting light. The simple-package LED has smaller height and width so as to be close to the pupil and the optical axis OA as much as possible and have a relatively larger light output angle. In one embodiment, the second surface 112 of the contact lens 12 has a light converging structure 112b corresponding to the light emitting elements 121 of the annular illumination module 12. The light converging structure 112b can converge a larger-angle direct illumination light source and allow it to pass through the pupil of the eyeball 20, resulted in increased illumination efficiency. In one embodiment, the light converging structure 112b is a convex surface. In one embodiment, the light converging structure is integrated with the light emitting element 121. In other words, the light emitting element 121 is a packaged LED containing a secondary optical structure.

According to the above-mentioned structural design, the contact-type ophthalmoscope of the present invention has a very compact structure. In one embodiment, the contact-type ophthalmoscope of the present invention further comprises a housing having a shape for handheld, such as a pistol shape. The contact-type ophthalmoscope of the present invention will be fabricated as a handheld device by arranging the contact lens 11, the annular illumination module 12, the imaging lens group 13 and the image capture module 14 inside the housing.

In one embodiment, the contact-type ophthalmoscope of the present invention further comprises a display module 15, which displays the image captured by the image capture module 14. It should be easily appreciated by the persons skilled in the art that the contact-type ophthalmoscope of the present invention may comprise a processing unit for computation, which may be integrated with or separated from the image capture module 14. The image captured by the image capture module 14 may be processed by the processing unit and then displayed on the display module 15. For example, the image captured by the image capture module 14 may be processed by the processing unit such as filtering noise, modifying contrast, and adjusting brightness to obtain better image quality. Since the technology of the processing unit has been well known by the persons skilled in the art, it will not be described in detail herein.

In one embodiment, the contact-type ophthalmoscope of the present invention further comprises a focus adjusting module 16. The focus adjusting module 16 drives mechanically or electronically the image capture module 14 to move linearly along the optical axis OA of the imaging lens group 13 to attain an appropriate focal length, as indicated by the arrow A in FIG. 1. As the focus adjusting module 16 moves the image capture module 14 linearly, the user can arbitrarily vary the back focus of the imaging lens group 13 without using other focus adjusting mechanisms, especially the nonlinear-compensation cam ring. Therefore, the imaging lens group 13 is simplified and allowed to have a greater tolerance. Thus is reduced the difficulty and cost of fabricating the imaging lens group 13. In one embodiment, the focus adjusting module 16 also drives at least one of the second lens group 132 and the third lens group 133 to move linearly along the optical axis OA of the imaging lens group 13 to attain an appropriate focal length.

In one embodiment, the contact-type ophthalmoscope of the present invention further comprises a connection port 17, whereby the contact-type ophthalmoscope can be physically connected with an external electronic device (not shown in the drawings) to transmit the images captured by the image capture module 14 to the external electronic device. In one embodiment, the connection port 17 is a Universal Serial Bus (USB).

In conclusion, the contact-type ophthalmoscope of the present invention makes the light source offset from the optical axis of the imaging system close to the pupil as much as possible such that the illumination field may be enlarged by using the direct illumination light sources with achieve a compact structure. Besides, the off-axis annular light source and the imaging system do not use common lenses and thus is exempted from the scattered light reflected from the lenses.

The embodiments described above are to demonstrate the technical thought and characteristics of the present invention to enable the persons skilled in the art to understand, make, and use the present invention. However, these embodiments are only to exemplify the present invention but not to limit the scope of the present invention. Any equivalent modification or variation according to the spirit of the present invention is to be also included within the scope of the present invention.

What is claimed is:

1. A contact-type ophthalmoscope, comprising:
   a contact lens having a first surface and a second surface, wherein said first surface is a concave surface configured for contacting an eyeball;
   an annular illumination module arranged close to said second surface of said contact lens and configured for providing a direct illumination source passing through a pupil of said eyeball and illuminate a fundus of the eyeball, wherein all or most of light generated by said direct illumination light source is directly incident onto said fundus of said eyeball without reflection by any artificial manipulation surface;
   an imaging lens group disposed in a central hollow portion of said annular illumination module and configured for converging reflected light from said fundus of said eyeball, wherein said central hollow portion of said annular illumination module has an inner diameter of 6-10 mm; and
   an image capture module configured for capturing said reflected light converged by said imaging lens group to form an image.

2. The contact-type ophthalmoscope according to claim 1, wherein said annular illumination module includes a plurality of light emitting elements arranged annularly and symmetrically or an annular light emitting element.

3. The contact-type ophthalmoscope according to claim 1, wherein said annular illumination module includes a plurality of first light emitting diodes and a plurality of second light emitting diodes, and wherein said first light emitting diodes are arranged annularly and symmetrically, and wherein said second light emitting diodes are also arranged annularly and symmetrically, and a central wavelength generated by said direct illumination source of said first light emitting diodes is different from a central wavelength generated by said direct illumination source of said second light emitting diodes.

4. The contact-type ophthalmoscope according to claim 1, wherein said annular illumination module includes a plurality of light emitting diodes arranged annularly and symmetrically, and said light emitting diodes have a simple package structure.

5. The contact-type ophthalmoscope according to claim 1, wherein said annular illumination module includes a plurality of light emitting diodes arranged annularly and symmetrically, and wherein said light emitting diodes have a package structure with a secondary optical structure.

6. The contact-type ophthalmoscope according to claim 1, wherein said second surface of said contact lens corresponding to said annular illumination module is provided with a light-converging structure configured for converging said direct illumination source to pass through said pupil of said eyeball.

7. The contact-type ophthalmoscope according to claim 1, wherein said second surface of said contact lens has a convex surface corresponding to said imaging lens group.

8. The contact-type ophthalmoscope according to claim 1, wherein said contact lens is made of a polymeric material.

9. The contact-type ophthalmoscope according to claim 1, wherein said contact lens is made of a soft biocompatible polymeric material.

10. The contact-type ophthalmoscope according to claim 1, wherein said imaging lens group includes a first lens group, a second lens group and a third lens group, which are arranged in sequence from said eyeball to said image capture module, and said first lens group converges said reflected light to form an intermediate image between said first lens group and said second lens group.

11. The contact-type ophthalmoscope according to claim 10, wherein at least one of said second lens group and said third lens group is arranged for being movable with respect to said first lens group.

12. The contact-type ophthalmoscope according to claim 10, wherein said second lens group includes at least two aspherical lenses.

13. The contact-type ophthalmoscope according to claim 10, wherein said third lens group includes at least two cemented doublet lenses, or a combination of a cemented doublet lens and a cemented triplet lens.

14. The contact-type ophthalmoscope according to claim 1 further comprising a display module configured for displaying said image captured by said image capture module.

15. The contact-type ophthalmoscope according to claim 1 further comprising a focus adjusting module configured for driving said image capture module or at least one lens group of said imaging module to move linearly along an optical axis of said imaging lens group.

16. The contact-type ophthalmoscope according to claim 1 further comprising a connection port configured for physically connecting to an external electronic device through said connection port to transmit said image captured by said image capture module to said external electronic device.

17. The contact-type ophthalmoscope according to claim 1 further comprising a housing having a shape designed for handheld, wherein said contact lens, said annular illumination module, said imaging lens group and said image capture module are arranged inside said housing to make said contact-type ophthalmoscope a handheld device.

* * * * *